US011369219B1

(12) United States Patent
Gitman et al.

(10) Patent No.: US 11,369,219 B1
(45) Date of Patent: Jun. 28, 2022

(54) TEMPERATURE CONTROLLED SLEEPING BAG

(71) Applicants: Jacob Gitman, Bay Harbor Island, FL (US); Victor Lander, Short Hills, NJ (US)

(72) Inventors: Jacob Gitman, Bay Harbor Island, FL (US); Victor Lander, Short Hills, NJ (US)

(*) Notice: Subject to any disclaimer, the term of this patent is extended or adjusted under 35 U.S.C. 154(b) by 0 days.

(21) Appl. No.: 17/461,358

(22) Filed: Aug. 30, 2021

(51) Int. Cl.
A47G 9/08 (2006.01)
A47G 9/02 (2006.01)
A61F 7/00 (2006.01)
F25B 21/02 (2006.01)
H05B 3/34 (2006.01)

(52) U.S. Cl.
CPC .......... *A47G 9/086* (2013.01); *A47G 9/0215* (2013.01); *A61F 7/0097* (2013.01); *F25B 21/02* (2013.01); *F25B 2321/02* (2013.01); *H05B 3/342* (2013.01)

(58) Field of Classification Search
CPC ..... A47G 9/086; A47G 9/0215; A61F 7/0097; H05B 3/342; F25B 21/02; F25B 2321/02; F25B 2321/023
USPC ..................... 62/3.2, 3.5; 219/212
See application file for complete search history.

(56) References Cited

U.S. PATENT DOCUMENTS

| 4,777,802 A | * | 10/1988 | Feher | A47G 9/0215 5/423 |
| 2010/0293715 A1 | * | 11/2010 | Sakamoto | A47G 9/0215 5/423 |
| 2018/0344044 A1 | * | 12/2018 | Parish | A47C 21/044 |
| 2021/0267379 A1 | * | 9/2021 | Youngblood | A61B 5/4812 |

* cited by examiner

Primary Examiner — Dana Ross
Assistant Examiner — James F Sims, III
(74) Attorney, Agent, or Firm — Henry M. Feiereisen LLC

(57) ABSTRACT

A sleeping bag has an electronically adjustable interior temperature by using cooled or heated air created by a heat exchanger based on Peltier effect and connected to the sleeping bag by flexible hoses via interfaces in exterior walls of the sleeping bag for directing the cooled or heated air received from heat exchanger into an interior of the sleeping bag.

8 Claims, 5 Drawing Sheets

TEMPERATURE CONTROLLED SLEEPING BAG

BACKGROUND OF THE INVENTION

Sleeping bags are generally designed to keep a human's body temperature within a sleeping bag at a consistently comfortable level during a time in which a human sleeps or rests in it. This attempt to keep a user consistently comfortable during resting is challenging in that the body heat tends to increase an interior temperature during sleep as well as occurrences of wide variations in outdoor temperatures during different seasons, which can vary from one hour to the next over a single sleeping period.

Therefore, the sleeping bag user may experience an uncomfortably high temperature during summertime outings or in other hot environment, or uncomfortably low interior temperature during the winter outing or in another cold weather environment.

Moreover, in order to withstand external elements sleeping bags are made with waterproof/airtight fabrics that make an interior natural heat exchange with external air difficult or almost impossible.

An ideal sleeping bag to keep humans sufficiently comfortable throughout a period of sleep would be a bag with an adjustable interior air temperature controlled by a user so as to accommodate external temperature changes, body heat variations, and personal preferences.

Thus, there is a need for a sleeping bag or a comforter, with air circulating properties that can be adjusted in accordance with personal preferences relative to an external weather environment.

Cooling and heating properties of solid state devices based on Peltier effect are the best to use for this purpose and are well known and widely used in scientific and industrial applications. There are several patents that describe attempts to use this effect to create a personal comfort environment, most of them using different wearable garments. For example, US Patent Application No. 20150237927 of Nelson describes "body envelopment for receiving the body of a user", which is essentially a set of Peltier elements located at different areas of human body.

In U.S. Pat. No. 8,397,517 to Monk, an air conditioning system for a motorcycle rider is presented, that uses a liquid heat exchanger based on Peltier effect to cool or heat up a garment wearer.

U.S. Pat. No. 10,842,205 to Lee describes the apparel thermo-regulatory system that actively heats or cools a wearer. In this system the Peltier elements are essentially weaved in the fabric that the user wears.

U.S. Pat. No. 10,299,525 to Buckman discloses a "heating or cooling unit stored in a backpack" in which the air blown by a fan is used for cooling or heating a helmet worn by the user.

U.S. Pat. Nos. 8,650,886 and 8,616,226 to Wilcoxon describe heat sinks with "a plurality of mechanically rigid tubing sections configured for being in thermal contact with the heat source and the heat sink." In this invention "The liquid is configured for being circulated within the loop for promoting transfer of thermal energy from the heat source to the heat sink via the loop."

It is therefore clear that currently available applications for portable versions of air conditioning cannot provide required performance applicable for sleeping bags users. Thus, it would be desirable to provide a method for cooling or heating a sleeping bag interior as well as a sleeping bag provided with corresponding means which eliminate the disadvantages of currently available sleeping bags.

SUMMARY OF THE INVENTION

Accordingly, it is an object of the present invention to provide a method for creating a comfortable environment for sleeping bag users, such as campers and tourists, which includes transfer of a cooled or heated air from an external heat exchanger that produces the hot or cold air via inlet and outlet couplings using flexible air hoses connected to the inlet and outlet couplings on the bag arranged in an outer airtight layer of the sleeping bag, both the inlet and outlet couplings been separable from the external heat exchanger providing an optional usage of the sleeping bag without an air conditioning system.

In the second aspect of this invention the method utilizes a closed loop sleeping bag ventilation system comprised of an interior space of the sleeping bag, an inlet coupling that has an opening into the interior space of the sleeping bag, and an outlet coupling that has an opening to the interior of the sleeping bag, providing an air circulation through the interior space and allowing used air to escape from the interior space through the outlet coupling and to be directed to the external heat exchanger for reuse to increase a system efficiency.

In the third aspect of this invention the method includes an addition of a regulated inlet provided for allowing a fresh external air to be mixed with a circulating air in a controllable amount.

According to the forth aspect of this invention a heating/cooling system for a sleeping bag user is provided, including a sleeping bag adapted to heat or to cool a sleeping bag user, and provided with an interior space created by an outer airtight thermally insulated layer and optional internal air permeable fabric and allowing an incoming air to freely circulate through the interior of the sleeping bag, and the sleeping bag is provided with an inlet coupling having an opening into the interior space of the sleeping bag and an outlet coupling with an opening into the interior space of the said bag, thermo-electric devices located externally and in the proximity to the sleeping bag and adapted to be electrically coupled to a source of direct current from a power supply, and having a first face exposed to an open air and a second face exposed to an air tunnel for operatively transferring heat using a set of Peltier elements from a first face to a second face or vice-versa depending upon a sense of the direct current.

The first face is thermally coupled to a thermally conductive element(s) (a heat sink(s)) exposed to atmosphere, and the second face being thermally coupled to a thermally conductive element (a heat sink) adapted to pass in a heat exchange relation a cooled or warmed up air inside of the air tunnel to atmosphere, wherein the air is directed to the inlet coupling in the sleeping bag via one air hose and returned from the sleeping bag outlet coupling to the heat exchanger via another air hose before passing again through the heat exchanger back to the inlet coupling in the said bag in a closed loop manner creating a closed loop air conditioning system for the interior space of the sleeping bag.

The system comprises the air space between inner air permeable layer and outer airtight layer of the sleeping bag, connections for circulating a working air from the outlet coupling of the bag to and through the thermally conductive element(s) (the heat sink(s)) of the Peltier thermal unit and back to the inlet coupling on the sleeping bag. Also, a fan is mounted on the Peltier heat exchange unit and adapted to cause a passage of reused air past the heat sink in a heat exchange relation therewith.

Preferably each of the sleeping bag outlets has a female interface and is connected to the heat exchanger via flexible air hoses provided with male interfaces at each coupling that fits snugly with the sleeping bag and heat exchanger outlets. Similarly, the heat exchanger has similar female interfaces that fit snugly with mail interface fitted to the other end of the air hoses. The outlet interface of the heat exchanger has additional short outlet opened to the external air with a passage controlled by using an adjustable damper, or a mechanically variable diaphragm, or a set of covers with different diameter holes in it, or any other means that allow to change a mixture of the fresh and recirculated air in the air stream coming into the heat exchanger from the sleeping bag. In the preferred embodiment all orifices have covers to prevent any foreign matter ingress.

While the user can simply turn the system on or off by using the switch on the heat exchanger, the system in the preferred embodiment is outfitted with a remote control module that can use a Bluetooth protocol to send commands to a corresponding Bluetooth receiver and a microcontroller in a Peltier power supply to increase or decrease the air temperature by changing the current through the Peltier elements, or change the airflow by controlling a fan voltage and to keep the bag interior in a comfortable zone.

DESCRIPTION OF PREFERRED EMBODIMENTS

It is known that an adult man radiates approximately 100-120 W of energy, mostly in the form of heat. During nature exploration and excursions the sleeping bag serves as a protection from weather elements. Typically, the sleeping bags are made using watertight and airtight materials for outer layers. These materials do not allow enough dissipation of the internally generated heat into the atmosphere, causing severe discomfort for the users, especially in warm and hot environment.

Figure 1:
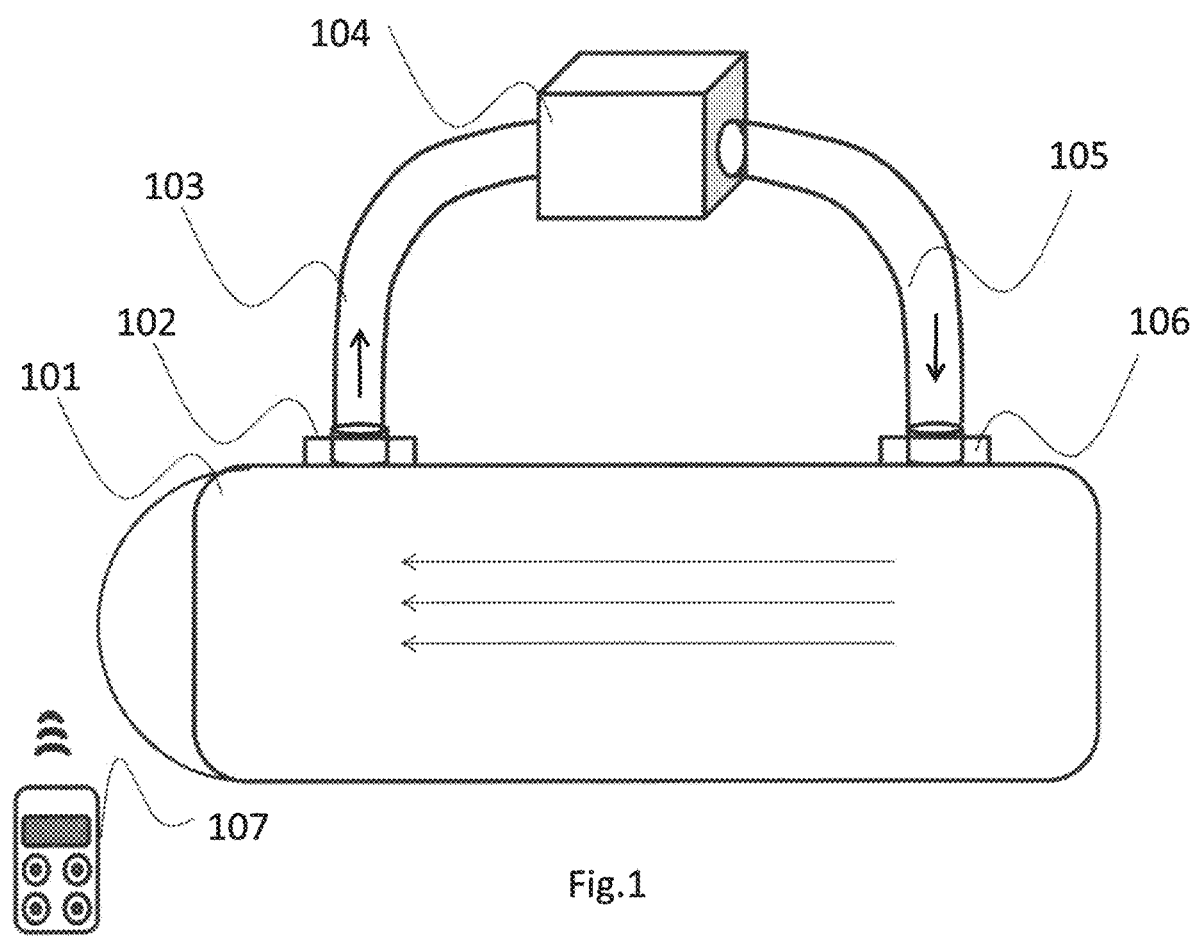
FIG. 1 of the drawings is a view showing a general diagram of a sleeping bag air conditioning system according to the present invention.

FIG. 1 demonstrates the proposed method for cooling or heating a sleeping bag interior to create a more comfortable environment for the user. A sleeping bag 101 is outfitted with two external couplings 102 and 106 that have openings into the interior of the sleeping bag. These couplings are connected via flexible air hoses 103 and 105 to a module 104 containing a Peltier effect heat exchanger, a power supply with a battery or AC, and controller units. The arrows indicate the air flow direction from the heat exchanger to the sleeping bag. The cooled air coming from the heat exchanger through the hose 103 enters an interior of the sleeping bag via the coupling 102 connected to the hose 103, circulates inside of the sleeping bag, and exits via the coupling 106 and is directed to the heat exchanger for reuse via the hose 105 connected to the coupling 106. The module 104 is an external module typically located in the proximity of the sleeping bag user, who can control the incoming air temperature and air volume via a remote control 107, equipped with a Bluetooth transmitter that can communicate with a heat exchanger microcontroller.

Figure 2:
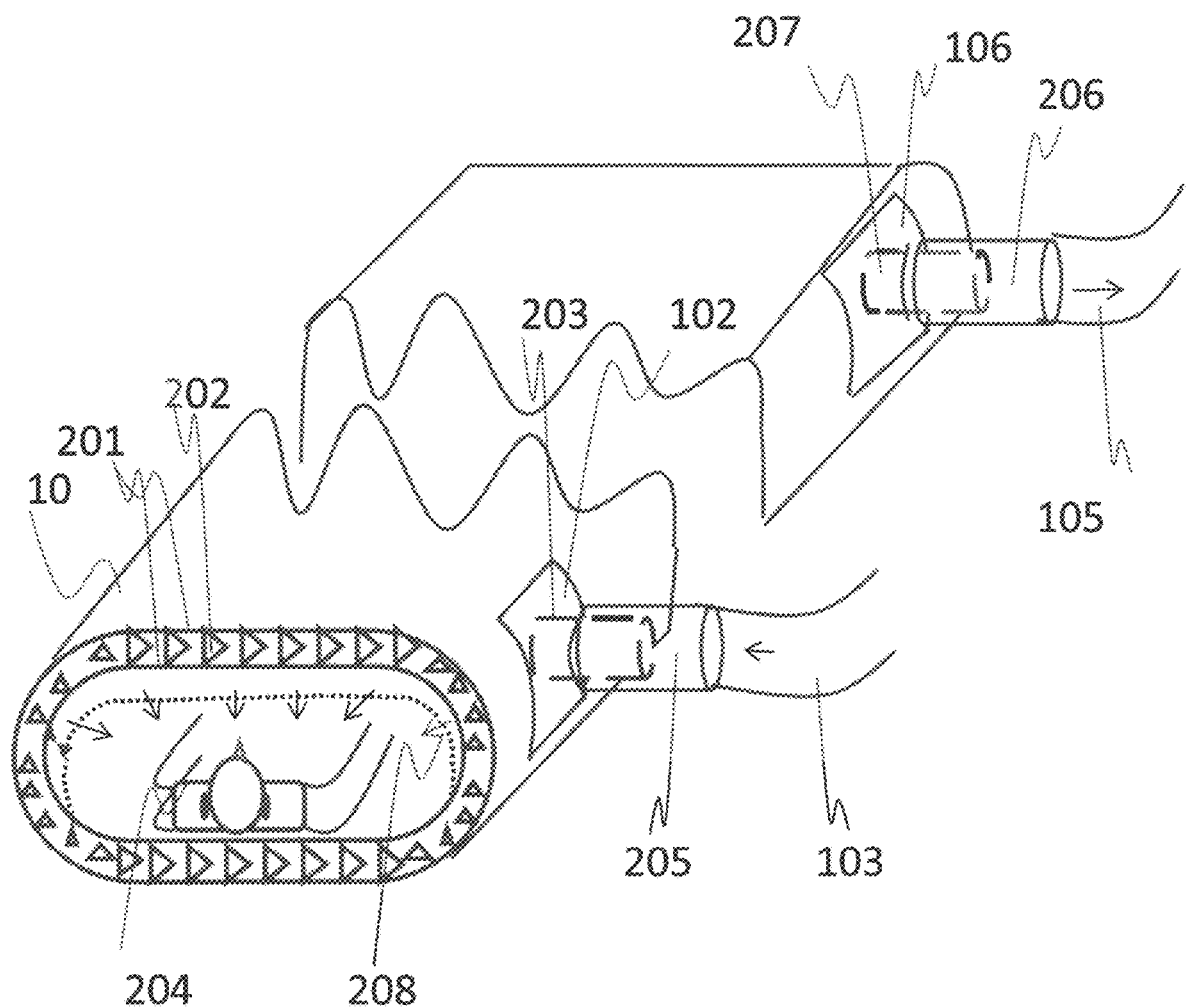
FIG. 2 of the drawings shows one possible embodiment of the sleeping bag air conditioning system according to the present invention, where an inlet and an outlet open up into an interior area of the sleeping bag, and inlet and outlet couplings are connected with air hoses.

FIG. 2 shows a cross-section of the proposed air conditioning system. A user 204 is positioned inside of the sleeping bag 101. The typical sleeping bag 101 consists of exterior and interior airtight and water-tight layers 201 with a thermal insulating material 202 stuffed between the layers. The inlet coupling 102 is shown with a separable male/female interface 205 with the air hose 103. A short inlet tube 203 provides fresh cooled air into the interior of the bag into the space between the exterior airtight layer 201 and interior air permeable fabric layer 208 allowing fresh cooled air to be evenly dissipated into the interior space. Similarly, the outlet coupling 106 is shown with a separable male/female interface 206 with the air hose 105. A used air is evacuated via an interior outlet opening equipped with a short plastic tube 207 and directed back to the heat exchanger by the hose 105. Such arrangement of interconnections allows the system to be easily assembled and disassembled.

Figure 3:
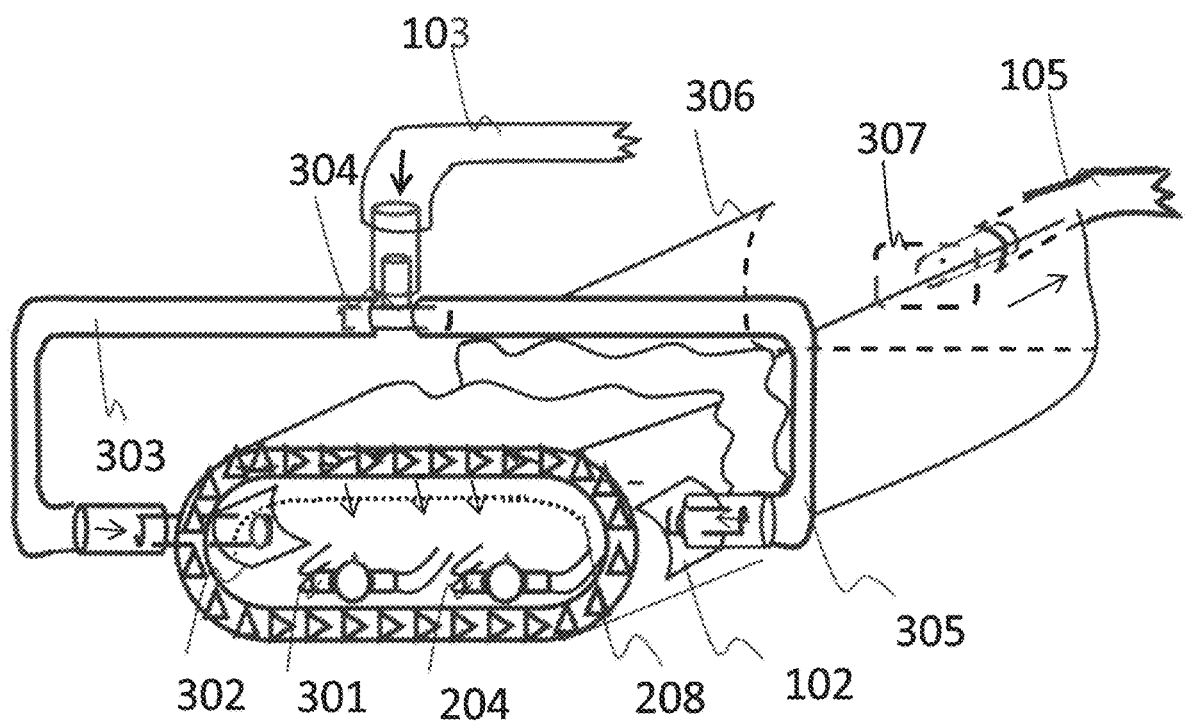
FIG. 3 of the drawings shows another possible embodiment for a wide sleeping bag for two-persons use according to the present invention, where an incoming conditioned air is supplied via two couplings on both sides of the sleeping bag into the space between exterior layer and interior air permeable fabric. The outlet coupling is located at the center of the bottom side of the bag.

FIG. 3 demonstrates another possible embodiment for a wide sleeping bag 306 for a two-person use, where an incoming conditioned air is supplied via two couplings on both sides of the sleeping bag and an outlet coupling is located at the center of the bottom side of the bag. In this embodiment two users 204 and 301 are located inside of the bag. The bag is outfitted with two inlet couplings, one on each side of the bag for even distribution of the air.

The air conditioned air is supplied from the hose 103 using a triple junction 304 connected to two hoses 303 and 305, which in turn are connected to two inlets 102 and 302 located on the sides of the bag and have orifices into the space between outer layer and internal air permeable fabric 20. Used air is evacuated from a single outlet 307 positioned in the center at the bottom of the bag. The outlet 307 is connected to the air hose 105 to direct the air back to the heat exchanger for recirculation FIG. 4 demonstrates a possible embodiment of the heat exchange assembly using Peltier elements. Solid state devices based on Peltier effect are well known in the industry for many years. One of the applications of Peltier elements as a compact heat pump is described in this application. Briefly, a Peltier element has two ceramic surfaces with semiconductor elements sandwiched in-between. When passing a DC current through the semiconductor elements, one of the surfaces becomes cold, while another surface becomes hot. Reversing the polarity of the DC current will change the operating mode of the Peltier element and the surface that was cold becomes hot and the surface that was hot becomes cold. The thermal pumping effect is increased with increasing the temperature difference between two surfaces.

In order to maximize the efficiency of the heat pumping effect, heat sinks 405 and 406 are thermo-conductively attached to each surface of the set of Peltier elements 404. The proposed heat exchanger is assembled on a circular tube 410 which serves as an air duct (or an air tunnel) and a mounting frame with openings for internal heat sinks 406, which are used for heating or cooling the air coming through the air tunnel 410.

Figure 4:
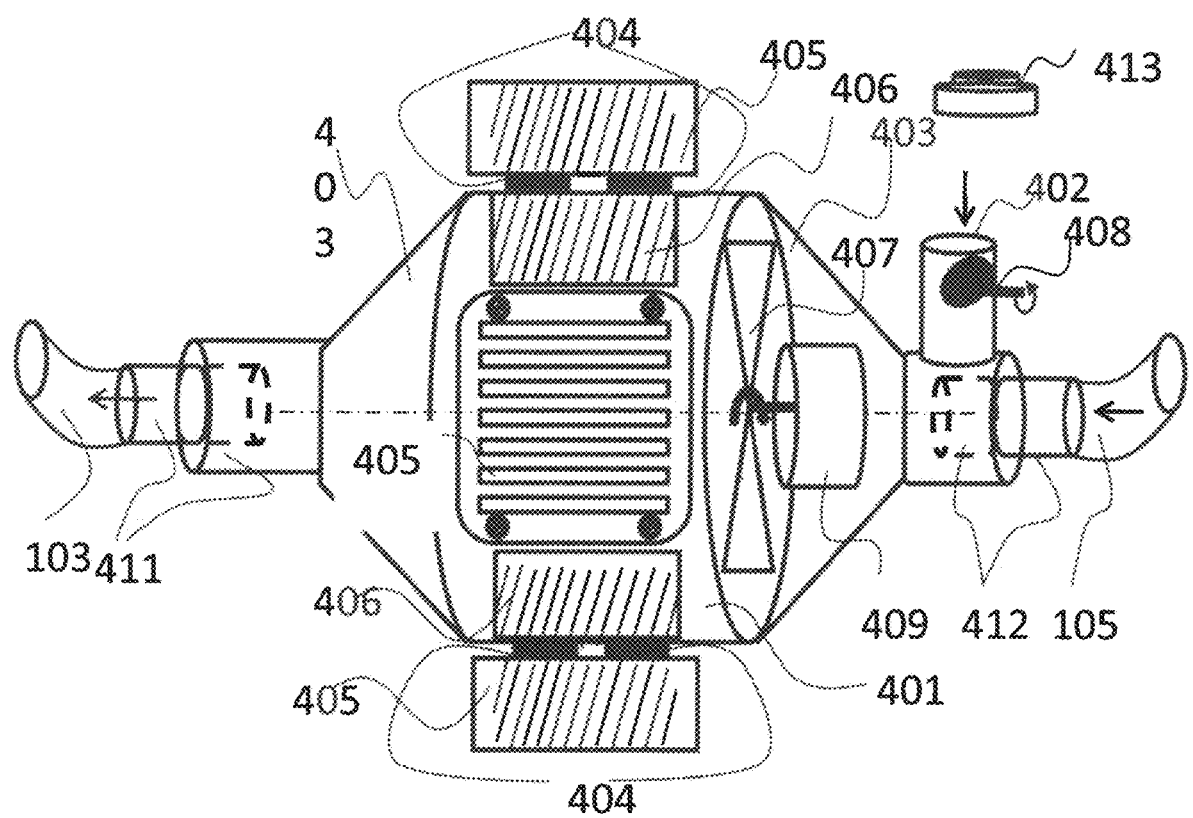
FIG. 4 of the drawings shows the cooling/heating heat exchanger assembly with Peltier elements and corresponding heat sinks and interfaces for incoming and outcoming air hoses according to the present invention.

The opposite surface of the Peltier elements is thermally connected to another set of heat sinks 405 and said elements are sandwiched between the heat sinks 406 and 405. The heat sinks 405 are exposed to the open air and the heat sinks 406 are exposed to the blowing air from the fan 407. In cooling operational mode, the fan 407 rotated by electrical motor 409 pushes warm air through a circular or square air tunnel 410, where air cools off by coming through and in contact with cold internal heat sinks 406 cooled by Peltier elements. The heat extracted from the air in the tunnel is transferred to the external heat sinks 405, which in turn are cooled by an external air. For interface with smaller diameter air hoses, the air tunnel 410 is fitted with conical transition parts 403, which have disconnectable female/male interfaces 411 and 412 with air hoses 103 and 105. During a dynamic thermal equilibrium, the system can constantly produce cooled air to cool the interior of the sleeping bag, while warming up the surrounding atmosphere. When the warming up of the interior is required, the polarity of DC current feeding the Peltier elements is switched to opposite, and the heat exchange process is reversed. FIG. 4 also shows a component 402, which is used to add a fresh air into the working air flow to optimize the comfort of the user. The amount of added air can be regulated, for example, by a damper 408, which can change the opening area by rotating the damper inside of the tube. Other designs such as diaphragms, caps, or registers also can be used. Protective caps 413 are used to cover all open outlets of the system during transportation or when the hoses are disconnected to prevent the foreign matter to get into the air passage.

Thermal solution for the assembly depends on the desirable airflow. For example, for dissipating q=200 Watts of heat typically produced by an adult person inside the slipping bag using heat sinks located inside of the air tunnel, the air flow can be estimated by the formula $$Q_f = 1.8 * q / \Delta T_c.$$

where
$Q_f$ is the air flow in cubic feet per minute;
q is amount of heat to be dissipated;
$\Delta T_c$ is the temperature gradient.

This formula for $\Delta T_c = 20$ C will give the amount of needed air flow $Q_f = 18$ CFM. There are many fans available in the industry that can provide the required air flow.

A mechanical assembly shown in FIG. 4 demonstrates the implementation of four heat exchange heat sinks on four sides of the air tunnel, which can be round or rectangular. A designer can use only two or even one heat sink for this purpose depending on the size of the system he designs.

Selection of the Peltier elements also depends on designer's preferences. For example, from reliability standpoint, several low power elements are more preferable than one high power element. For power transfer of 200-300 W the optimal amount of Peltier components is four to eight. As an example, it can be assumed that it is needed to transfer 200 W of heat, using 8 Peltier elements. For that requirement each element must be capable to transfer 25 W of heat. Assuming that each element will operate at 50% of maximum capacity, it will need the elements specified at $Q_{max}=50$ W for each element and $\Delta T=75$ C. A typical Peltier element with these parameters has outside dimensions 40 mm×40 mm×4.6 mm. FIG. 4 shows a Peltier elements assembly 404 sandwiched between the two heat sinks 405 and 406 providing required temperature gradient between Peltier surfaces and making a heat pump operating mode possible.

Figure 5:
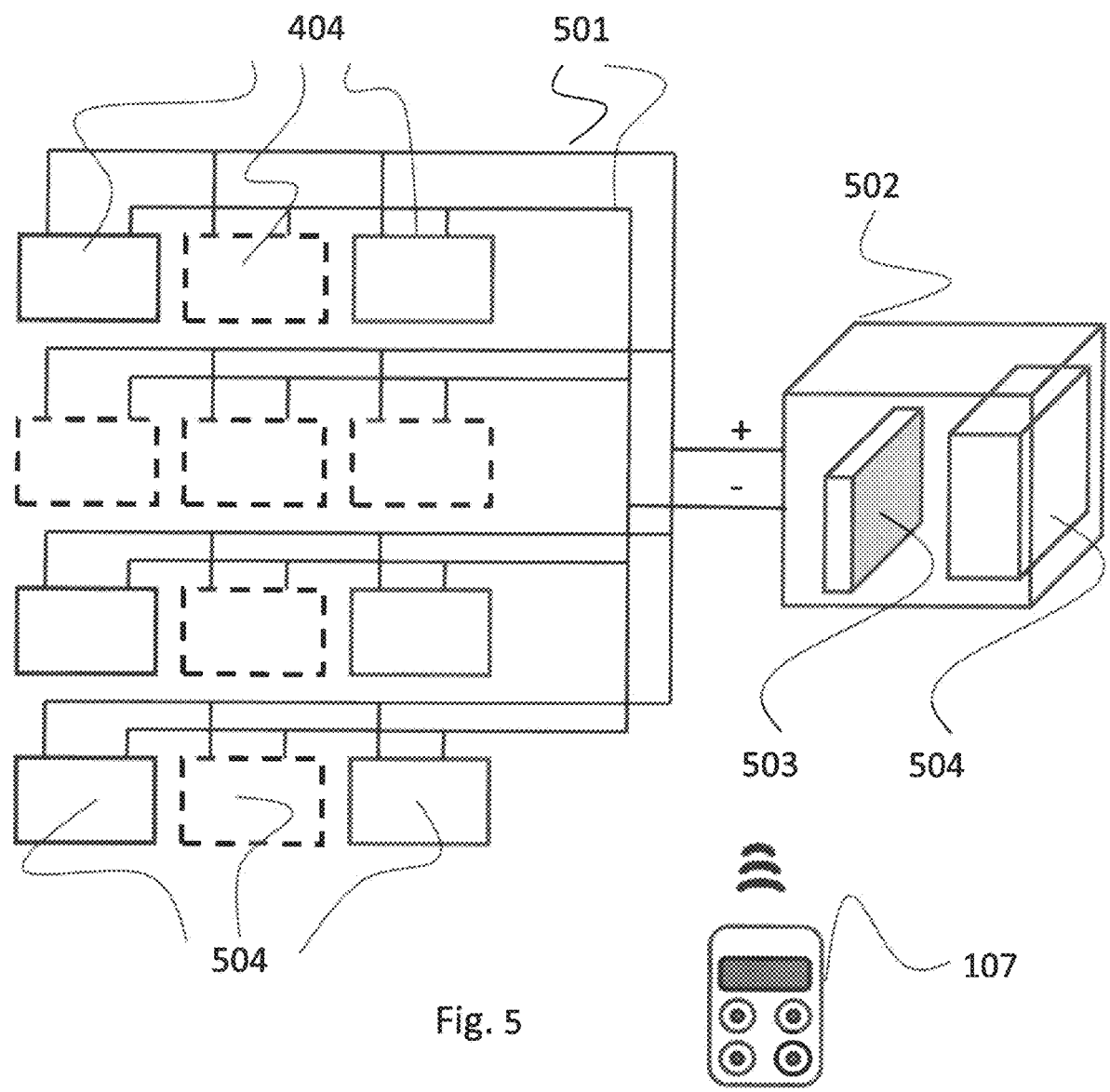
FIG. 5 of the drawings shows a possible embodiment for an electrical power interconnection according to the present invention, with a remote control of incoming air temperature and an air flow.

FIG. 5 shows a preferred embodiment of an electrical connection of the proposed invention. The elements 404 can be connected in parallel, in series, or in a hybrid configuration. The parallel connections using a wiring diagram 501 is shown in FIG. 5. A typical maximum operating voltage for the element with $Q_{max}=50$ W is 20 V and a current $I_{max}=4$ A. Operating elements at 75% of maximum power will result in a current of 3 A and in total power supply minimum requirements for eight elements of 400 W. Considering a very small amount of power required for the fan and auxiliary electronics and efficiency of Peltier elements, the total power of 400-800 W will be sufficient.

Control of the temperature and air flow of the system can be done remotely using the digital remote control 107 equipped with a Bluetooth chip set. The remote unit will communicate with a microcontroller 503 that can adjust the voltage on Peltier elements and/or the voltage on the fan to increase or decrease the incoming air temperature or to increase or decrease the voltage on the fan to change the air flow. The control module 502 contains a battery, a microcontroller, a power conditioning unit for operation from external AC or internal battery and all other necessary electronics in the block 504.

Many variations on proposed system realizing the method for air conditioning of sleeping bag are also possible to persons skilled in the art in view of the present disclosure.

What is desired to be protected by Letters Patent is set forth in the appended claims.

What we claim is:

1. A sleeping bag comprising a heating or cooling system for heating or cooling of a sleeping bag interior and for free circulation of an incoming cool or warm air through the sleeping bag interior; an inlet coupling having an opening into an interior space created between an interior layer made of air permeable fabric and an exterior thermos-isolating layer of the sleeping bag for even distribution of incoming air into an interior space of the sleeping bag; an outer coupling having an opening into the interior space of the sleeping bag for evacuation of a used air; a thermo-electric unit based on Peltier effect, located externally and in a proximity to the sleeping bag and having an internal set of heat sinks and external set of heat sinks and adapted to be electrically coupled to a source of direct current from an external source for transferring heat from the internal set of heat sinks to the external set of heat sinks and vice-versa depending upon sensing the direct current coming through a set of Peltier elements, with a first face of the Peltier elements being thermally coupled to a metal heat sink exposed to atmosphere, and a second face of the Peltier elements being thermally coupled to a heat sink located in an air tunnel adapted to pass in a heat exchange relation a cooled air or a warmed up air which directed to the inlet coupling in the sleeping bag, circulated through the interior of sleeping bag and exiting through the outlet coupling of the sleeping bag before passing back to a heat exchanger for air conditioning creating a closed loop air conditioning system for a user of the sleeping bag, wherein said system comprising an air space of an interior of the sleeping bag and connections for circulating air from the outlet coupling to and through an internal heat sink of a Peltier effect thermal unit and back to the inlet coupling of the sleeping bag; and a fan mounted on a Peltier heat exchange unit and adapted to cause passage of a reused air through an air tunnel with the heat sinks in a heat exchange relation therewith.

2. A sleeping bag of claim 1, wherein each of the inlet coupling and the outlet coupling has external interfaces and a coupling member connected to air hoses providing connections in the heating and cooling system, wherein one the coupling members being a male member and another of the coupling members being a female member.

3. A sleeping bag of claim 1, further comprising an inlet hose interface; and an additional opening provided in the heat exchange unit and having a variable size opening to a fresh air, providing a desirable mixture of the fresh air and the recirculated air.

4. A sleeping bag of claim 1, wherein each of the couplings is provided with a cover to prevent ingress of dirt or another foreign matter.

5. A sleeping bag of claim 1, further comprising of a temperature control system including a remote unit allowing user to communicate via Bluetooth protocol with a corresponding microcontroller in a heat exchanger located in the vicinity of the sleeping bag and capable of changing a temperature or a flow of air for a comfortable environment.

6. A sleeping bag of claim 5, wherein the heat exchanger contains a micro controller that can communicate remotely and control a current through Peltier elements to increase or decrease an incoming air temperature according to commands of a user.

7. A sleeping bag of claim 5, wherein the heat exchanger contains a micro controller that can communicate with a remote unit and can control a voltage of a fan in order to increase or decrease an air flow according to commands of a user.

8. A sleeping bag of claim 1, further comprising a protection system having an automatically operable circuit to protect a battery or an external AC power supply from overload when an excessive current is above a safety range.

* * * * *